United States Patent [19]

Wahl et al.

[11] Patent Number: 5,654,182

[45] Date of Patent: *Aug. 5, 1997

[54] FLP-MEDIATED GENE MODIFICATION IN MAMMALIAN CELLS, AND COMPOSITIONS AND CELLS USEFUL THEREFOR

[75] Inventors: Geoffrey M. Wahl; Stephen V. O'Gorman, both of San Diego, Calif.

[73] Assignee: The Salk Institute for Biological Studies, La Jolla, Calif.

[*] Notice: The portion of the term of this patent subsequent to Nov. 3, 2013, has been disclaimed.

[21] Appl. No.: 484,324

[22] Filed: Jun. 7, 1995

Related U.S. Application Data

[63] Continuation of Ser. No. 147,912, Nov. 3, 1993, which is a continuation of Ser. No. 666,252, Mar. 8, 1991, abandoned.

[51] Int. Cl.$^6$ .............. C12N 15/00; C12N 15/85
[52] U.S. Cl. .............. 435/172.1; 435/172.3; 435/320.1; 435/352; 435/353; 435/354; 435/364; 435/366; 514/44; 536/23.1; 536/23.74; 536/24.1; 536/24.2; 935/70; 935/52; 935/33; 935/6; 935/34; 800/2
[58] Field of Search .............. 435/172.3, 320.1, 435/240.2, 172.1; 514/44; 536/23.1, 23.74, 24.1, 24.2; 935/52, 55, 56, 57, 68, 69, 70, 71, 72, 33

[56] References Cited

U.S. PATENT DOCUMENTS 4,959,317  9/1990  Sauer ................... 435/172.3
4,997,757  3/1991  Schiestl ................ 435/172.1

OTHER PUBLICATIONS

Webster's II New Riverside University Dictionary, Soukhanov et al. (eds) 1984, Houghton Mifflin Company, Boston, MA p. 917.

Pamiter, R.D. 1986, Ann. Rev. Genet. 20: 465–499.

Golic et al., 1989, Cell 59: 499–509.

Primary Examiner—Christopher S. F. Low
Attorney, Agent, or Firm—Gray Cary Ware & Freidenrich; Stephen E. Reiter

[57] ABSTRACT

A gene activation/inactivation and site-specific integration system has been developed for mammalian cells. The invention system is based on the recombination of transfected sequences by FLP, a recombinase derived from Saccharomyces. In several cell lines, FLP has been shown to rapidly and precisely recombine copies of its specific target sequence. For example, a chromosomally integrated, silent β-galactosidase reporter gene was activated for expression by FLP-mediated removal of intervening sequences to generate clones of marked cells. Alternatively, the reverse reaction can be used to target transfected DNA to specific chromosomal sites. These results demonstrate that FLP can be used, for example, to mosaically activate or inactivate transgenes for a variety of therapeutic purposes, as well as for analysis of vertebriate development.

14 Claims, 3 Drawing Sheets

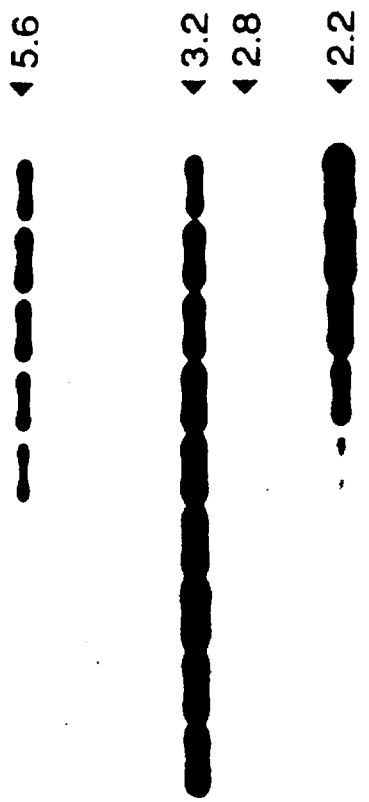
FIG.2B
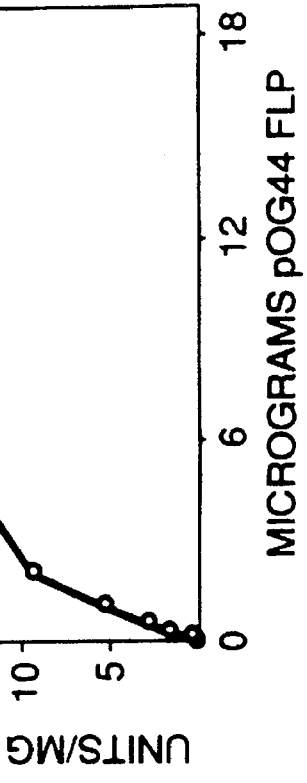
FIG.2C
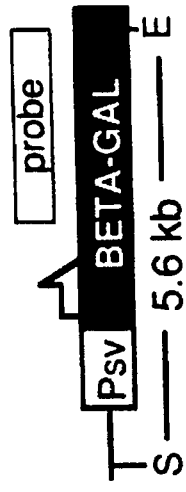
FIG.2A pFRTβGAL
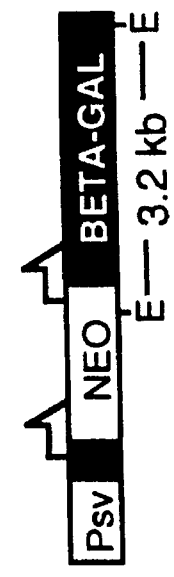
pNEOβGAL
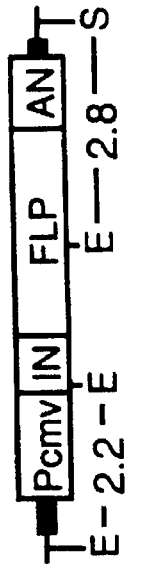
pOG44 FLP

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 1380 base pairs
        ( B ) TYPE: nucleic acid
        ( C ) STRANDEDNESS: single
        ( D ) TOPOLOGY: linear ( i i ) MOLECULE TYPE: DNA (genomic)

( v i i ) IMMEDIATE SOURCE:
        ( B ) CLONE: NATIVE FLP ( i x ) FEATURE:
        ( A ) NAME/KEY: CDS
        ( B ) LOCATION: 1..1269

( x i ) SEQUENCE DESCRIPTION: SEQ ID NO:1:

| | | | | | | | | | | | | | | | | |
|---|---|---|---|---|---|---|---|---|---|---|---|---|---|---|---|---|
| ATG | CCA | CAA | TTT | GAT | ATA | TTA | TGT | AAA | ACA | CCA | CCT | AAG | GTG | CTT | GTT | 48 |
| Met | Pro | Gln | Phe | Asp | Ile | Leu | Cys | Lys | Thr | Pro | Pro | Lys | Val | Leu | Val | |
| 1 | | | | 5 | | | | | 10 | | | | | 15 | | |
| CGT | CAG | TTT | GTG | GAA | AGG | TTT | GAA | AGA | CCT | TCA | GGT | GAG | AAA | ATA | GCA | 96 |
| Arg | Gln | Phe | Val | Glu | Arg | Phe | Glu | Arg | Pro | Ser | Gly | Glu | Lys | Ile | Ala | |
| | | | 20 | | | | | 25 | | | | | 30 | | | |
| TTA | TGT | GCT | GCT | GAA | CTA | ACC | TAT | TTA | TGT | TGG | ATG | ATT | ACA | CAT | AAC | 144 |
| Leu | Cys | Ala | Ala | Glu | Leu | Thr | Tyr | Leu | Cys | Trp | Met | Ile | Thr | His | Asn | |
| | | 35 | | | | | 40 | | | | | 45 | | | | |
| GGA | ACA | GCA | ATC | AAG | AGA | GCC | ACA | TTC | ATG | AGC | TAT | AAT | ACT | ATC | ATA | 192 |
| Gly | Thr | Ala | Ile | Lys | Arg | Ala | Thr | Phe | Met | Ser | Tyr | Asn | Thr | Ile | Ile | |
| | 50 | | | | | 55 | | | | | 60 | | | | | |
| AGC | AAT | TCG | CTG | AGT | TTC | GAT | ATT | GTC | AAT | AAA | TCA | CTC | CAG | TTT | AAA | 240 |
| Ser | Asn | Ser | Leu | Ser | Phe | Asp | Ile | Val | Asn | Lys | Ser | Leu | Gln | Phe | Lys | |
| 65 | | | | | 70 | | | | | 75 | | | | | 80 | |
| TAC | AAG | ACG | CAA | AAA | GCA | ACA | ATT | CTG | GAA | GCC | TCA | TTA | AAG | AAA | TTG | 288 |
| Tyr | Lys | Thr | Gln | Lys | Ala | Thr | Ile | Leu | Glu | Ala | Ser | Leu | Lys | Lys | Leu | |
| | | | | 85 | | | | | 90 | | | | | 95 | | |
| ATT | CCT | GCT | TGG | GAA | TTT | ACA | ATT | ATT | CCT | TAC | TAT | GGA | CAA | AAA | CAT | 336 |
| Ile | Pro | Ala | Trp | Glu | Phe | Thr | Ile | Ile | Pro | Tyr | Tyr | Gly | Gln | Lys | His | |
| | | | 100 | | | | | 105 | | | | | 110 | | | |
| CAA | TCT | GAT | ATC | ACT | GAT | ATT | GTA | AGT | AGT | TTG | CAA | TTA | CAG | TTC | GAA | 384 |
| Gln | Ser | Asp | Ile | Thr | Asp | Ile | Val | Ser | Ser | Leu | Gln | Leu | Gln | Phe | Glu | |
| | | 115 | | | | | 120 | | | | | 125 | | | | |
| TCA | TCG | GAA | GAA | GCA | GAT | AAG | GGA | AAT | AGC | CAC | AGT | AAA | AAA | ATG | CTT | 432 |
| Ser | Ser | Glu | Glu | Ala | Asp | Lys | Gly | Asn | Ser | His | Ser | Lys | Lys | Met | Leu | |
| | 130 | | | | | 135 | | | | | 140 | | | | | |
| AAA | GCA | CTT | CTA | AGT | GAG | GGT | GAA | AGC | ATC | TGG | GAG | ATC | ACT | GAG | AAA | 480 |
| Lys | Ala | Leu | Leu | Ser | Glu | Gly | Glu | Ser | Ile | Trp | Glu | Ile | Thr | Glu | Lys | |
| 145 | | | | | 150 | | | | | 155 | | | | | 160 | |
| ATA | CTA | AAT | TCG | TTT | GAG | TAT | ACT | TCG | AGA | TTT | ACA | AAA | ACA | AAA | ACT | 528 |
| Ile | Leu | Asn | Ser | Phe | Glu | Tyr | Thr | Ser | Arg | Phe | Thr | Lys | Thr | Lys | Thr | |
| | | | | 165 | | | | | 170 | | | | | 175 | | |
| TTA | TAC | CAA | TTC | CTC | TTC | CTA | GCT | ACT | TTC | ATC | AAT | TGT | GGA | AGA | TTC | 576 |
| Leu | Tyr | Gln | Phe | Leu | Phe | Leu | Ala | Thr | Phe | Ile | Asn | Cys | Gly | Arg | Phe | |
| | | | 180 | | | | | 185 | | | | | 190 | | | |
| AGC | GAT | ATT | AAG | AAC | GTT | GAT | CCG | AAA | TCA | TTT | AAA | TTA | GTC | CAA | AAT | 624 |
| Ser | Asp | Ile | Lys | Asn | Val | Asp | Pro | Lys | Ser | Phe | Lys | Leu | Val | Gln | Asn | |
| | | 195 | | | | | 200 | | | | | 205 | | | | |
| AAG | TAT | CTG | GGA | GTA | ATA | ATC | CAG | TGT | TTA | GTG | ACA | GAG | ACA | AAG | ACA | 672 |
| Lys | Tyr | Leu | Gly | Val | Ile | Ile | Gln | Cys | Leu | Val | Thr | Glu | Thr | Lys | Thr | |
| | 210 | | | | | 215 | | | | | 220 | | | | | |
| AGC | GTT | AGT | AGG | CAC | ATA | TAC | TTC | TTT | AGC | GCA | AGG | GGT | AGG | ATC | GAT | 720 |
| Ser | Val | Ser | Arg | His | Ile | Tyr | Phe | Phe | Ser | Ala | Arg | Gly | Arg | Ile | Asp | |
| 225 | | | | | 230 | | | | | 235 | | | | | 240 | |
| CCA | CTT | GTA | TAT | TTG | GAT | GAA | TTT | TTG | AGG | AAT | TCT | GAA | CCA | GTC | CTA | 768 |
| Pro | Leu | Val | Tyr | Leu | Asp | Glu | Phe | Leu | Arg | Asn | Ser | Glu | Pro | Val | Leu | |
| | | | | 245 | | | | | 250 | | | | | 255 | | |
| AAA | CGA | GTA | AAT | AGG | ACC | GGC | AAT | TCT | TCA | AGC | AAT | AAA | CAG | GAA | TAC | 816 |
| Lys | Arg | Val | Asn | Arg | Thr | Gly | Asn | Ser | Ser | Ser | Asn | Lys | Gln | Glu | Tyr | |
| | | | 260 | | | | | 265 | | | | | 270 | | | |
| CAA | TTA | TTA | AAA | GAT | AAC | TTA | GTC | AGA | TCG | TAC | AAT | AAA | GCT | TTG | AAG | 864 |
| Gln | Leu | Leu | Lys | Asp | Asn | Leu | Val | Arg | Ser | Tyr | Asn | Lys | Ala | Leu | Lys | |
| | | 275 | | | | | 280 | | | | | 285 | | | | |
| AAA | AAT | GCG | CCT | TAT | TCA | ATC | TTT | GCT | ATA | AAA | AAT | GGC | CCA | AAA | TCT | 912 |
| Lys | Asn | Ala | Pro | Tyr | Ser | Ile | Phe | Ala | Ile | Lys | Asn | Gly | Pro | Lys | Ser | |
| | 290 | | | | | 295 | | | | | 300 | | | | | |
| CAC | ATT | GGA | AGA | CAT | TTG | ATG | ACC | TCA | TTT | CTT | TCA | ATG | AAG | GGC | CTA | 960 |
| His | Ile | Gly | Arg | His | Leu | Met | Thr | Ser | Phe | Leu | Ser | Met | Lys | Gly | Leu | |
| 305 | | | | | 310 | | | | | 315 | | | | | 320 | |

```
ACG GAG TTG ACT AAT GTT GTG GGA AAT TGG AGC GAT AAG CGT GCT TCT    1008
Thr Glu Leu Thr Asn Val Val Gly Asn Trp Ser Asp Lys Arg Ala Ser
            325             330             335

GCC GTG GCC AGG ACA ACG TAT ACT CAT CAG ATA ACA GCA ATA CCT GAT    1056
Ala Val Ala Arg Thr Thr Tyr Thr His Gln Ile Thr Ala Ile Pro Asp
        340             345             350

CAC TAC TTC GCA CTA GTT TCT CGG TAC TAT GCA TAT GAT CCA ATA TCA    1104
His Tyr Phe Ala Leu Val Ser Arg Tyr Tyr Ala Tyr Asp Pro Ile Ser
        355             360             365

AAG GAA ATG ATA GCA TTG AAG GAT GAG ACT AAT CCA ATT GAG GAG TGG    1152
Lys Glu Met Ile Ala Leu Lys Asp Glu Thr Asn Pro Ile Glu Glu Trp
        370             375             380

CAG CAT ATA GAA CAG CTA AAG GGT AGT GCT GAA GGA AGC ATA CGA TAC    1200
Gln His Ile Glu Gln Leu Lys Gly Ser Ala Glu Gly Ser Ile Arg Tyr
385             390             395             400

CCC GCA TGG ATT GGG ATA ATA TCA CAG GAG GTA CTA GAC TAC CTT TCA    1248
Pro Ala Trp Ile Gly Ile Ile Ser Gln Glu Val Leu Asp Tyr Leu Ser
            405             410             415

TCC TAC ATA AAT AGA CGC ATA TAAGTACGCA TTTAAGCATA AACACGCACT       1299
Ser Tyr Ile Asn Arg Arg Ile
                420

ATCCCGTTCT TCTCATGTAT ATATATATAC AGGCAACACG CAGATATAGG TGCGACGTGA  1359

ACAGTGAGCT GTATGTGCGC A                                            1380
```

( 2 ) INFORMATION FOR SEQ ID NO:2:

( i ) SEQUENCE CHARACTERISTICS:
        ( A ) LENGTH: 423 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Pro Gln Phe Asp Ile Leu Cys Lys Thr Pro Pro Lys Val Leu Val
 1               5                  10                  15

Arg Gln Phe Val Glu Arg Phe Glu Arg Pro Ser Gly Glu Lys Ile Ala
                20                  25                  30

Leu Cys Ala Ala Glu Leu Thr Tyr Leu Cys Trp Met Ile Thr His Asn
            35                  40                  45

Gly Thr Ala Ile Lys Arg Ala Thr Phe Met Ser Tyr Asn Thr Ile Ile
        50                  55                  60

Ser Asn Ser Leu Ser Phe Asp Ile Val Asn Lys Ser Leu Gln Phe Lys
65                  70                  75                  80

Tyr Lys Thr Gln Lys Ala Thr Ile Leu Glu Ala Ser Leu Lys Lys Leu
                85                  90                  95

Ile Pro Ala Trp Glu Phe Thr Ile Ile Pro Tyr Tyr Gly Gln Lys His
            100                 105                 110

Gln Ser Asp Ile Thr Asp Ile Val Ser Ser Leu Gln Leu Gln Phe Glu
        115                 120                 125

Ser Ser Glu Glu Ala Asp Lys Gly Asn Ser His Ser Lys Lys Met Leu
130                 135                 140

Lys Ala Leu Leu Ser Glu Gly Glu Ser Ile Trp Glu Ile Thr Glu Lys
145                 150                 155                 160

Ile Leu Asn Ser Phe Glu Tyr Thr Ser Arg Phe Thr Lys Thr Lys Thr
                165                 170                 175

Leu Tyr Gln Phe Leu Phe Leu Ala Thr Phe Ile Asn Cys Gly Arg Phe
            180                 185                 190
```

| | | | | | | | | | | | | | |
|---|---|---|---|---|---|---|---|---|---|---|---|---|---|
| Ser | Asp | Ile 195 | Lys | Asn | Val | Asp | Pro 200 | Lys | Ser | Phe | Lys 205 | Leu | Val | Gln | Asn |
| Lys | Tyr 210 | Leu | Gly | Val | Ile | Ile 215 | Gln | Cys | Leu | Val | Thr 220 | Glu | Thr | Lys | Thr |
| Ser 225 | Val | Ser | Arg | His | Ile 230 | Tyr | Phe | Phe | Ser | Ala 235 | Arg | Gly | Arg | Ile | Asp 240 |
| Pro | Leu | Val | Tyr | Leu 245 | Asp | Glu | Phe | Leu | Arg 250 | Asn | Ser | Glu | Pro | Val 255 | Leu |
| Lys | Arg | Val | Asn 260 | Arg | Thr | Gly | Asn | Ser 265 | Ser | Ser | Asn | Lys | Gln 270 | Glu | Tyr |
| Gln | Leu | Leu 275 | Lys | Asp | Asn | Leu | Val 280 | Arg | Ser | Tyr | Asn | Lys 285 | Ala | Leu | Lys |
| Lys | Asn 290 | Ala | Pro | Tyr | Ser | Ile 295 | Phe | Ala | Ile | Lys | Asn 300 | Gly | Pro | Lys | Ser |
| His 305 | Ile | Gly | Arg | His | Leu 310 | Met | Thr | Ser | Phe | Leu 315 | Ser | Met | Lys | Gly | Leu 320 |
| Thr | Glu | Leu | Thr | Asn 325 | Val | Val | Gly | Asn | Trp 330 | Ser | Asp | Lys | Arg | Ala 335 | Ser |
| Ala | Val | Ala | Arg 340 | Thr | Thr | Tyr | Thr | His 345 | Gln | Ile | Thr | Ala | Ile 350 | Pro | Asp |
| His | Tyr | Phe 355 | Ala | Leu | Val | Ser | Arg 360 | Tyr | Tyr | Ala | Tyr | Asp 365 | Pro | Ile | Ser |
| Lys | Glu 370 | Met | Ile | Ala | Leu | Lys 375 | Asp | Glu | Thr | Asn | Pro 380 | Ile | Glu | Glu | Trp |
| Gln 385 | His | Ile | Glu | Gln | Leu 390 | Lys | Gly | Ser | Ala | Glu 395 | Gly | Ser | Ile | Arg | Tyr 400 |
| Pro | Ala | Trp | Ile | Gly 405 | Ile | Ile | Ser | Gln | Glu 410 | Val | Leu | Asp | Tyr | Leu 415 | Ser |
| Ser | Tyr | Ile | Asn 420 | Arg | Arg | Ile | | | | | | | | | |

( 2 ) INFORMATION FOR SEQ ID NO:3:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

```
GAAGTTCCTA TTCTCTAGAA AGTATAGGAA CTTC                                34
```

( 2 ) INFORMATION FOR SEQ ID NO:4:

( i ) SEQUENCE CHARACTERISTICS:
        ( A ) LENGTH: 68 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

```
GATCCCGGGC TACCATGGAG AAGTTCCTAT TCCGAAGTTC CTATTCTCTA GAAAGTATAG    60
GAACTTCA                                                             68
```

FLP-MEDIATED GENE MODIFICATION IN MAMMALIAN CELLS, AND COMPOSITIONS AND CELLS USEFUL THEREFOR

This application is a continuation application of U.S. patent application Ser. No. 08/147,912, filed Nov. 3, 1993, now pending, which is in turn a continuation application of U.S. patent application Ser. No. 07/666,252, filed Mar. 8, 1991, now abandoned, the entire contents of each of which are hereby incorporated by reference herein.

This invention relates to recombinant DNA technology. In a particular aspect, this invention relates to methods for the site-specific recombination of DNA in mammalian cells or host mammalian organisms. In another aspect, the present invention relates to novel DNA constructs, as well as compositions, cells and host organisms containing such constructs. In yet another aspect, the present invention relates to methods for the activation and/or inactivation of expression of functional genes. In a further aspect, the present invention relates to methods for the introduction of DNA into specific sites in the genome of mammalian cells. In a still further aspect, the present invention relates to gene therapy methods. In still another aspect, the present invention relates to means for the recovery of transfected DNA from a cell or host organism. In a still further aspect, the present invention relates to assay methods.

BACKGROUND OF THE INVENTION

Many recent manipulations of gene expression involve the introduction of transfected genes (transgenes) to confer some novel property upon, or to alter some intrinsic property of, mammalian cells or organisms. The efficacy of such manipulations is often impaired by such problems as the inability to control the chromosomal site of transgene integration; or the inability to control the number of copies of a transgene that integrate at the desired chromosomal site; or by difficulties in controlling the level, temporal characteristics, or tissue distribution of transgene expression; or by the difficulty of modifying the structure of transgenes once they are integrated into mammalian chromosomes.

Transgenes are often introduced into mammalian cells or organisms to determine which components of a transgene are required for specific qualitative or quantitative alterations of the host system. Since both chromosomal position and copy number are major determinants of transgene function, the usefulness of these analyses is limited because current techniques for efficiently introducing transgenes into mammalian hosts result in the insertion of a variable number of transgene copies at random chromosomal positions. It is, therefore, difficult (if not impossible) to compare the effects of one transgene to those of another if the two transgenes occupy different chromosomal positions and are present in the genome at different copy numbers. Considerably more refined analyses would be possible if one could routinely introduce single copies of a variety of transgenes into a defined chromosomal position.

The spatial or temporal characteristics of transgene expression is difficult to control in intact organisms. The restricted expression of transgenes is potentially of great interest, as this technique can be employed for a variety of therapeutic applications, e.g., for the selective interruption of a defective gene, for the alteration of expression of a gene which is otherwise over-expressed or under-expressed, for the selective introduction of a gene whose product is desirable in the host, for the selective removal or disruption of a gene whose expression is no longer desired in the host, and the like.

Transgene expression is typically governed by a single set of control sequences, including promoters and enhancers which are physically linked to the transgenes (i.e., cis-acting sequences). Considerably greater expression control could be achieved if transgene expression could be placed under the binary control of these cis-acting sequences, plus an additional set of sequences that were not physically linked to the transgenes (i.e., trans-acting sequences). A further advantage would be realized if the transient activity of these trans-acting functions resulted in a stable alteration in transgene expression. In this manner, it would be possible, for example, to introduce into a host a transgene whose expression would have lethal or deleterious effects if it was constitutively expressed in all cells. This would be accomplished by delaying the expression of the transgene to a specific time or developmental stage of interest, or by restricting the expression of the transgene to a specific subset of the cell population.

It is currently difficult (if not impossible) to precisely modify the structure of transgenes once they have been introduced into mammalian cells. In many applications of transgene technology, it would be desirable to introduce the transgene in one form, and to then be able to modify the transgene in a defined manner. By this means, transgenes could be activated or inactivated or the sequences which control transgene expression could be altered by either removing sequences present in the original transgene or by inserting additional sequences into the transgene.

Previous descriptions of recombinase-mediated rearrangement of chromosomal sequences in Drosophila and mammalian cells have not directly addressed the question of whether site-specific recombinases could routinely create a functional translational reading frame. Moreover, the reported efficiency of the prior art recombinase system, in the only other description of site-specific recombination in mammalian cells reported to date [based on Cre recombinase, described by Sauer and Henderson in *Nucleic Acids Research*, Vol. 17:147 (1989)] appears to be quite low.

BRIEF DESCRIPTION OF THE INVENTION

In accordance with the present invention, we have developed a system for the selective modification of chromosomal or extrachromosomal DNA in mammalian cells. Selective modification can involve the insertion of one DNA into another DNA (e.g., to create a hybrid gene, to activate a gene, to inactivate a gene, and the like), or the removal of specific DNA molecule(s) from other DNA molecule(s) containing the DNA to be removed (e.g., to inactivate a gene, to bring desired DNA fragments into association with one another, and the like).

The recombination system of the present invention is based on site-specific recombinase, FLP. In one application of the invention recombination system, FLP-mediated removal of intervening sequences is required for the formation of a functional gene. Expression of the functional gene therefore, falls under the control of both the regulatory sequences associated with the functional gene and also under the control of those sequences which direct FLP expression.

The reverse of the above-described process, i.e., the FLP-mediated introduction of DNA, provides a convenient and selective means to introduce DNA into specific sites in mammalian chromosomes.

FLP-mediated recombination of marker genes provides a means to follow the fate of various sequences over the course of development and/or from generation-togeneration. The recombination event creates a functional marker gene. This gain-of-function system can be used for lineage analyses in a wide variety of tissues in different organisms. Prior to FLP-mediated recombination, the marker gene is normally silent, i.e., the phenotype typical of the marker is not observed. In the absence of FLP, spontaneous recombination to produce functional marker occurs only at very low frequencies. In the presence of FLP, functional marker is efficiently produced. In addition, this gain-of-function system is heritable and is easily detected by simple histochemical assays. For example, in transgenic mice, the lineages in which recombination is to occur can be controlled by appropriate selection of the promoters used to drive FLP expression. This could include promoters that are only transiently active at a developmental stage that substantially precedes overt cell differentiation. Since transcription of the marker gene is controlled by regulatory sequences associated therewith, functional marker genes can be expressed at later developmental stages, after cell differentiation has occurred. By this means, it is possible to construct a map for mammalian development that correlates embryonic patterns of gene expression with the organization of mature tissues.

BRIEF DESCRIPTION OF THE FIGURES

In FIG. 1A, FLP-mediated introduction of DNA is illustrated, while in FIG. 1B, FLP-mediated removal of intervening sequences is illustrated.

FIGS. 2A, 2B, and 2C. FIG. 2A presents schematic diagrams of the expression vectors pFRTβGAL, pNEOβGAL, and pOG44 FLP. FIG. 2B presents a Southern blot of Hirt lysates prepared from 293 (human embryonic kidney) cells transfected with one microgram of pNEOβGAL and varying amounts of the pOG44 FLP expression vector. FIG. 2C graphically presents the β-galactosidase activities in the same transfections shown in part B, referred to above.

FIG. 3A, at the top, presents a schematic of the pattern of plasmid integration in E25 deduced from Southern blot analysis. FIG. 3A, in the middle, presents the predicted pattern for β-galactosidase positive subclones of E25 if precise recombination across the FLP-recombination target sites occurs. FIG. 3A, at the bottom, presents the predicted pattern for β-galactosidase negative, neomycin resistant subclones of E25B2 after FLP mediated insertion of pOG45. FIG. 3B presents an analysis of genomic DNA from a cell line with a single integrated copy of pNEOβGAL (i.e., CVNEOβGAL/E25, designated as E25), two derivative β-galactosidase-positive subclones (designated as E25B1 and E25B2), and two subclones derived from E25B2 after transfection with pOG45 (designated as B2N1 and B2N2).

DETAILED DESCRIPTION OF THE INVENTION

Figure 1A:
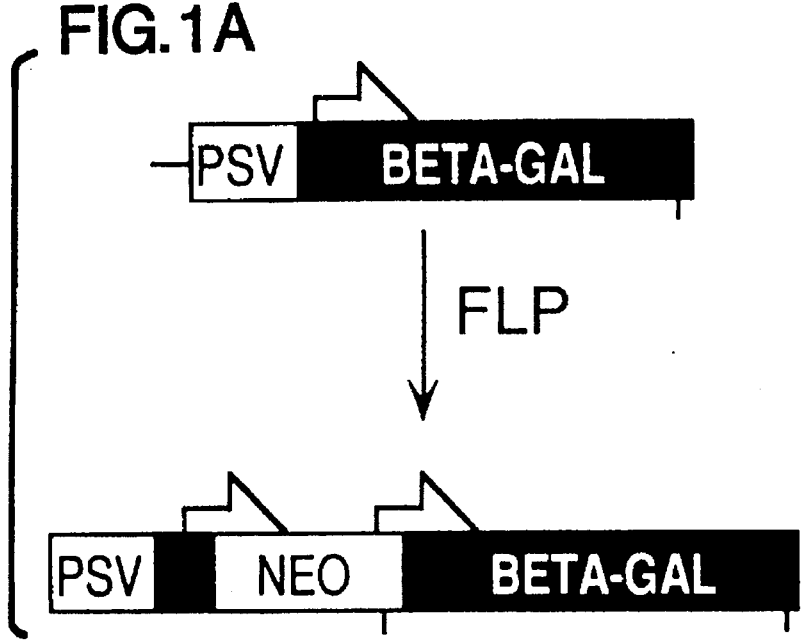
FIGS. 1A and 1B are schematic diagrams of FLP-mediated recombination events.
Figure 1A:
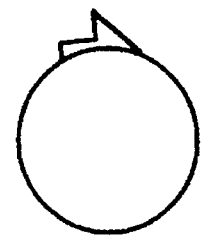

In accordance with the present invention, there is provided a mammalian recombination system comprising:
(i) FLP recombinase, or a nucleotide sequence encoding same, and
(ii) a first DNA comprising a nucleotide sequence containing at least one FLP recombination target site.

In accordance with another embodiment of the present invention, there are provided novel DNA constructs useful for the introduction of DNA into the genome of a transfected organism, said DNA construct comprising, as an autonomous fragment:

(a) at least one FLP recombination target site,
(b) at least one restriction endonuclease recognition site,
(c) at least one marker gene,
(d) a bacterial origin of replication, and optionally
(e) a mammalian cellular or viral origin of DNA replication.

In accordance with yet another embodiment of the present invention, there are provided novel DNA constructs useful for the rescue of DNA from the genome of a transfected organism, said DNA construct comprising, as an autonomous fragment, in the following order, reading from 5' to 3' along said fragment:

(a) a first FLP recombination target site,
(b) an insert portion comprising, in any suitable sequence:
  (1) at least one restriction endonuclease recognition site,
  (2) at least one marker gene,
  (3) a bacterial origin of replication, and optionally
  (4) a mammalian cellular or viral origin of DNA replication, and
(c) a second FLP recombination target site in tandem with said first FLP recombination target site.

In addition, there are provided methods for the recovery of transfected DNA from the genome of a transfected organism employing the above-described constructs.

In accordance with still another embodiment of the present invention, there is provided a method for the assembly of a functional gene (which is then suitable for activation of expression), in mammalian cells, by recombination of individually inactive gene segments derived from one or more gene(s) of interest, wherein each of said segments contains at least one recombination target site, said method comprising:

contacting said individually inactive gene segments with a FLP recombinase, under conditions suitable for recombination to occur, thereby providing a DNA sequence which encodes a functional gene of interest.

In accordance with a further embodiment of the present invention, there is provided a method for the disruption of functional gene(s) of interest, thereby inactivating expression of such gene(s), in mammalian cells, wherein said gene(s) of interest contain at least one FLP recombination target site, said method comprising contacting said gene(s) of interest with:

(i) a DNA segment which contains at least one FLP recombination target site, and
(ii) FLP recombinase;

wherein said contacting is carried out under conditions suitable for recombination to occur between said gene and said DNA segment, thereby disrupting the gene(s) of interest and rendering said gene(s) non-functional.

In accordance with a still further embodiment of the present invention, there is provided a method for the precisely targeted integration of DNA into the genome of a host organism, said method comprising:

(i) introducing a FLP recombination target site into the genome of cells which are compatible with the cells of the subject,
(ii) introducing a first DNA comprising a nucleotide sequence containing at least one FLP recombination target site therein into the FLP recombination target site in the genome of said cells by contacting said cells with said first DNA and FLP recombinase, and thereafter
(iii) introducing the cells produced by the process of step (ii) into said subject, wherein the resulting cells and/or organism have the optional ability to have DNA reproducibly and repetitively inserted into and/or recovered from the host cells and/or organism.

In accordance with another aspect of the present invention, there are provided mammalian cells, wherein the genomic DNA of said cells contain at least one FLP recombination target site therein.

In accordance with yet another aspect of the present invention, there are provided transgenic, non-human mammals, wherein said mammals contain at least one FLP recombination target site in the genomic DNA thereof.

In accordance with yet another aspect of the present invention, there is provided a method for the site-specific integration of transfected DNA into the genome of the above-described cells and/or transgenic, non-human mammals, said method comprising:

(i) contacting said genome with:
  (a) FLP recombinase, and
  (b) a first DNA comprising a nucleotide sequence containing at least one FLP recombination target site therein; and thereafter
(ii) maintaining the product of Step (i) under conditions suitable for site-specific integration of said DNA sequence to occur at the FLP recombination target site in said genome.

In accordance with a further aspect of the present invention, there is provided a method for the analysis of the development of a mammal, said method comprising:

(a) providing a transgenic mammal comprising:
  (i) an expression construct encoding FLP under the control of a conditional promoter, and
  (ii) a reporter construct under the control of the same or a different promoter, wherein said reporter construct encodes a functional or non-functional reporter gene product, and wherein said construct contains at least one FLP recombination target site therein,
  wherein the functional expression of the functional reporter gene is disrupted when said FLP recombination event occurs, or
  wherein the functional expression of the non-functional reporter gene commences when said FLP recombination event occurs; and
(b) following the development of said mammal to determine when expression of functional reporter gene product either commences or is disrupted.

In accordance with a still further aspect of the present invention, there is provided a co-transfection assay FLP-mediated recombination, said assay comprising:

(a) co-transfecting a host mammalian cell with:
  (i) a FLP expression plasmid, and
  (ii) a reporter plasmid comprising a reporter gene inactivated by the presence of at least one recombination target site; and
(b) monitoring said host cell under a variety of conditions for the gain of expression of functional reporter gene product.

FLP recombinase is a protein which catalyzes a site-specific recombination reaction that is involved in amplifying the copy number of the 2 μ plasmid of *S.cerevisiae* during DNA replication. FLP protein has been cloned and expressed in *E.coli* [see, for example, Cox, in proceedings of the National Academy of Sciences U.S.A., Vol. 80:4223–4227 (1983)], and has been purified to near homogeneity [see, for example, Meyer-Lean, et al., in Nucleic Acids Research, Vol. 15: 6469–6488 (1987)]. FLP recombinases contemplated for use in the practice of the present invention are derived from species of the genus Saccharomyces. Preferred recombinases employed in the practice of the present invention are derived from strains of *Saccharomyces cerevisiae*. Especially preferred recombinases employed in the practice of the present invention are proteins having substantially the same amino acid sequence as set forth in Sequence I.D. No. 2, as encoded, for example, by Sequence I.D. No. 1, or the sequence set forth by Hartley and Donelson, Nature 286:860 (1980).

The FLP recombination target site (sometimes referred to herein as "FRT") has also been identified as minimally comprising two 13 base-pair repeats, separated by an 8 base-pair spacer, as follows:

-Spacer-

5'-GAAGTTCCTATTC[TCTAGAAA]GTATAGGAACTTC-3'XbaI
site (SEQ ID NO:3)

The nucleotides in the above "spacer" region can be replaced with any other combination of nucleotides, so long as the two 13 base-pair repeats are separated by 8 nucleotides. The actual nucleotide sequence of the spacer is not critical, although those of skill in the art recognize that, for some applications, it is desirable for the spacer to be asymmetric, while for other applications, a symmetrical spacer can be employed. Generally, the spacers of the FLP recombination target sites undergoing recombination with one another will be the same.

Figure 1B:
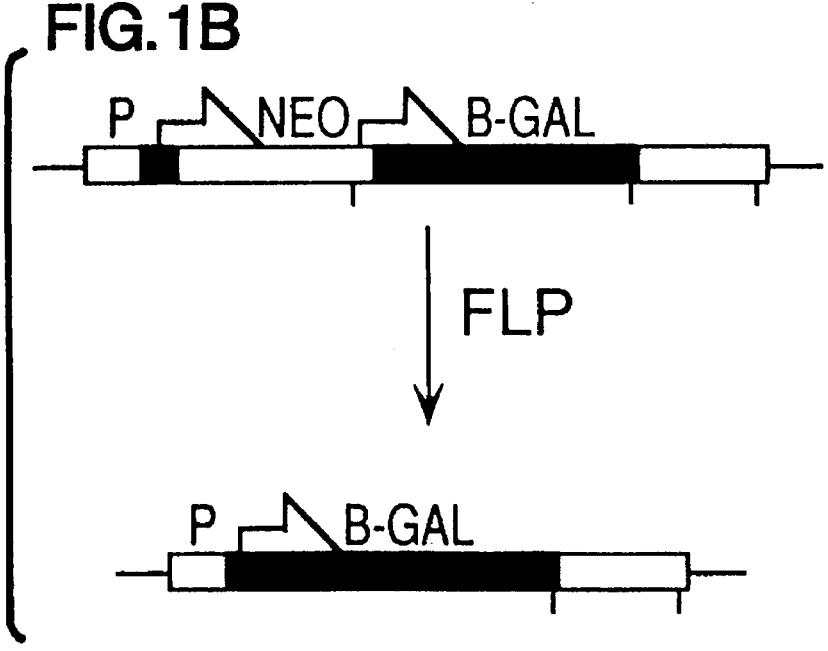
Figure 1B:
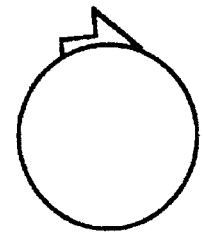

As schematically illustrated in FIG. 1A, contact of genomic DNA containing a FLP recombination target site (shown as the linear Psv-BETA-GAL construct) with a vector containing a FLP recombination target site, in the presence of the protein, FLP recombinase, results in recombination that forms a new genomic sequence wherein the vector sequences have been precisely incorporated into the genome of the host. The reverse of this process is shown schematically in FIG. 1B, wherein a genomic sequence or construct containing two tandemly oriented FLP recombination target sites, upon contacting with FLP, is recombined and the FLP recombination target site-bounded fragment is excised as a circular molecule.

Genes of interest contemplated for use in the practice of the present invention can be selected from genes which provide a readily analyzable functional feature to the host cell and/or organism, e.g., visible markers (such as β-galactosidase, thymidine kinase, tyrosinase, and the like), selectable markers, (such as markers useful for positive and negative selection, e.g., genes for antibiotic resistance), as well as other functions which alter the phenotype of the recipient cells, and the like.

The first DNA employed in the practice of the present invention can comprise any nucleotide sequence containing at least one FLP recombination target site, which will precisely define the locus at which FLP-mediated recombination will occur. The nucleotide sequence can comprise all or part of a gene of interest, as well as other sequences not necessarily associated with any known gene. Optionally, for ease of later recovery of the gene of interest (in "activated" or modified form), the first DNA can optionally contain a second FLP recombination target site.

The second DNA employed in the practice of the present invention is selected from at least a second portion of the first gene of interest or at least a portion of a second gene of interest (including an intact form of a second gene of interest). When the second DNA is at least a second portion of the first gene of interest, the site-specific recombination of the present invention may act to provide a functional combination of the different portions of the first gene of interest. Alternatively, when the second DNA is at least a portion of a second gene of interest, the site-specific recombination of the present invention may act to provide a functional hybrid gene, which produces a product which is not identical with either the product of the first gene or the second gene. As yet another alternative, when the second DNA is a portion of a second gene, the site-specific recombination of the present invention may act to disrupt the function of the first gene of interest. Based on the nature of the first DNA and the second DNA, as well as the mode of interaction between the two, the site-specific interaction of the present invention may create or disrupt a feature which is colorimetrically detectable, immunologically detectable, genetically detectable, and the like.

In accordance with the present invention, assembly of a functional expression unit is achieved in any of a variety of ways, e.g., by association of the gene of interest with a functional promoter, by assembly of common gene fragments to produce a complete functional gene (which, in combination with its promoter, comprises a functional expression unit), or assembly of diverse gene fragments from diverse sources to produce a functional, hybrid gene (which, in combination with a promoter, comprises a functional expression unit), and the like. Upon assembly of a functional expression unit as described herein, expression of the functional gene to produce a protein product can be activated in the usual manner. In the absence of FLP-mediated recombination, activation of expression would fail to produce a functional protein product.

In accordance with the present invention, dis-assembly of a functional expression unit is achieved in any of a variety of ways, e.g., by dis-associating the gene of interest from a functional promoter, by dis-assembly (e.g., disruption) of the functional gene (e.g., by introduction of DNA which renders the entire sequence non-functional), by removal of a substantial portion of the coding region of said gene, and the like. Upon dis-assembly of a functional expression unit as described herein, expression of the functional gene product under the conditions required prior to gene dis-assembly is no longer possible. The ability of the expression unit to be activated for expression has therefore been disrupted. The gene in this situation can be said to be inactivated, since activation of expression is not possible.

Individually inactive gene segments contemplated for use in the practice of the present invention are fragments which, alone, do not encode functional products. Such fragments can be derived from a first gene of interest alone, or from both a first and second gene of interest DNA fragments.

When gene inactivation is desired, the gene of interest can be disrupted with a DNA fragment which throws the gene of interest out of reading frame (e.g., an insert wherein the number of nucleotides is not a multiple of 3). Alternatively, the gene of interest can be disrupted with a fragment which encodes a segment which is substantially dissimilar with the gene of interest so as to render the resulting product non-functional. As yet another alternative, the gene of interest can be disrupted so as to dis-associate the gene of interest from the transcriptional control of the promoter with which it is normally associated.

The introduction of DNA, e.g., DNA encoding FLP recombination target sites, into the genome of target cells can be accomplished employing standard techniques, e.g., transfection, microinjection, electroporation, infection with retroviral vectors, and the like.

Introduction of protein, e.g., FLP recombinase protein, to host cells and/or organisms can be accomplished by standard techniques, such as for example, injection or microinjection, transfection with nucleotide sequences encoding FLP, and the like.

When employed for gene therapy of an intact organism, introduction of transgenic cells into the subject is accomplished by standard techniques, such as for example, grafting, implantation, and the like.

Mammalian cells contemplated for use in the practice of the present invention include all members of the order Mammalia, such as, for example, human cells, mouse cells, rat cells, monkey cells, hamster cells, and the like.

Host organisms contemplated for use in the practice of the present invention include each of the organism types mentioned above, with the proviso, however, that no claim is made to genetically modified human hosts (although the present invention contemplates methods for the treatment of humans).

Once FLP recombinase (or DNA encoding same) and DNA containing at least one FLP recombination target site have been introduced into suitable host cells/organisms, the cells/host organisms are maintained under conditions suitable for the site-specific recombination of DNA. Such conditions generally involve conditions required for the viability of the host cell or organism. For in vitro manipulations, conditions employed typically involve low concentrations of a variety of buffers having a pH of between about 5–9 and ionic strengths in the range of about 50–350 mM. See, for example, Senecoff, et al., in *Journal of Molecular Biology*, Vol. 201:405–421 (1988).

In accordance with a particular aspect of the present invention, a co-transfection assay has been developed which can be used to characterize FLP-mediated recombination of extrachromosomal DNA in a variety of cell lines. Cells are co-transfected with an expression construct and a "reporter" plasmid that is a substrate for the recombinase. The expression construct encodes a FLP recombinase protein. The reporter plasmid encodes either a functional reporter gene containing at least one recombination target site therein, or a non-functional reporter gene containing at least one recombination target site therein. Upon expression of FLP by the expression construct, the functional reporter gene will be rendered non-functional, or the non-functional reporter gene will be rendered functional. Thus, the activity of the expression construct can be assayed either by recovering the reporter plasmid and looking for evidence of recombination at the DNA level, or by preparing cytoplasmic extracts and looking for evidence of recombination at the protein level (i.e., by measuring the expression of reporter gene activity generated by the recombined reporter). Such assays are described in greater detail in Example 1 below.

The invention will now be described in greater detail by reference to the following non-limiting examples.

EXAMPLES

Example 1-Co-transfection Assays.

The co-transfection assay used to characterize FLP-mediated recombination of extrachromosomal DNA involved transfection of cells with an expression construct and a "reporter" plasmid that was a substrate for the recombinase. The activity of the expression construct could be assayed either by recovering the reporter plasmid and looking for molecular evidence of recombination at the DNA level, or by preparing cytoplasmic extracts and looking for evidence of recombination at the protein level (i.e., by measuring β-galactosidase activity generated by recombined reporter).

The pNEOβGAL reporter plasmid used for these assays was derived from pFRTβGAL (FIG. 2A). In the Figure, half-arrows indicate positions of FLP recombination target (FRT) sites; E and S designate EcoRI and ScaI restriction sites, respectively; Psv designates early promoter from SV40; BETA-GAL designates the β-galactosidase structural sequence; NEO designates neomycin expression cassette; Pcmv designates the cytomegalovirus immediate early promoter; IN designates an intron; FLP designates a FLP coding sequence; AN designates an SV40 adenylation cassette; thin lines represent vector sequences; and the sizes of restriction fragments are indicated in kb.

pFRTβGAL contains a version of the bacterial β-galactosidase sequence modified by insertion of a FLP recombination target site, or FRT, within the protein coding sequence immediately 3' to the translational start. The oligonucleotide used for the construction of pFRTβGAL was:

5'-GATCCCGGGCTACCATGGA•GAAGTTCCTATTC•CGAAG-TTCCTATTC(TCTAGA)AAGTATAGGAACTTCA-3'. (SEQ ID NO:4)

This oligonucleotide contains an in-frame start codon, minimal FRT site, and an additional copy of the 13-bp FRT repeat [oXXXo]; the XbaI site within the FRT spacer is enclosed in parentheses. The linker was inserted between the BamHI and HindIII sites of pSKS105 (M. J. Casadaban, A. Martin-Arias, S. K. Shapira, and J. Chou, *Meth. Enzymol.* 100, 293 (1983)) and the LacZ portion of modified gene was cloned into a pSV2 vector. The neomycin cassette used for construction of pNEOβGAL was an XhoI to BamHI fragment from pMClneo-polyA (K. Thomas and M. Capecchi, *Cell* 51:503 (1987)) cloned between copies of the J3 FRT site in pUC19.

The FRT consists of two inverted 13-base-pair (bp) repeats and an 8-bp spacer that together comprise the minimal FRT site, plus an additional 13-bp repeat which may augment reactivity of the minimal substrate. The β-galactosidase translational reading frame was preserved upon insertion of the FRT site, and the resulting plasmid, pFRTβGAL, generated robust activity in mammalian cells (Table 1).

pNEOβGAL was constructed by cutting pFRTβGAL in the middle of the FRT site with XbaI and then inserting an XbaI fragment consisting of two half-FRT sites flanking a neomycin transcription unit. This created intact FRTs on either side of the neomycin cassette and rendered the β-galactosidase transcription unit inactive (Table 1). Precise FLP-mediated recombination of the FRTs caused the excision of the neomycin cassette, recreated the parental pFRTβGAL plasmid, and restored β-galactosidase expression.

Co-transfection of cells with a fixed amount of pNEOβGAL reporter plasmid and increasing amounts of the pOG44 FLP expression vector generated increasing amounts of recombined reporter plasmid and consequently, increased levels of β-galactosidase activity. Molecular evidence for FLP-mediated recombination was obtained by recovering plasmids 36 hours after transfection, followed by endonuclease treatment (with EcoRI and ScaI) and Southern blotting (see FIG. 2B; employing as a probe the fragment of pFRTβGAL indicated at the top of FIG. 2A). Lysates of cells from cotransfections that included the pOG44 FLP expression vector showed a signal at 5.6 kb, the position at which recombined reporter (equivalent to pFRTβGAL) would run, and a 3.2 kb signal that was generated by unrecombined pNEOβGAL reporter (FIG. 2A). The 5.6 kb band intensity was proportional to the amount of FLP expression plasmid included in the transfection. The 5.6 kb band was not seen in cotransfections in which a non-FLP plasmid was substituted for the FLP expression vector (FIG. 2B) or in transfections that contained only pOG44 (and no reporter plasmid). pOG44 generated additional signals at 2.2 kb and 2.8 kb because the plasmid used in its construction contained EcoRI and EcoRI-ScaI fragments of such length.

pOG44 consists of the cytomegalovirus immediate early promoter from pCDM8 [see Aruffo and Seed in Proc. Natl Acad. Sci., USA 84:8573 (1987)], a 5' leader sequence and synthetic intron from pMLSIScat [see Huang and Gorman in Nucl. Acids Res. 18:937 (1990)], the FLP coding sequence (bp 5568–6318 and 1–626 of the 2 μm circle, [see Hartley and Donelson, *Nature* 286:860 (1980)]' and the SV40 late region polyadenylation signal from pMLSIScat. The following silent nucleotide substitutions were introduced into the structural FLP sequence using the polymerase chain reaction: C for T at position 5791, G for A at 5794, G for C at 5800, C for T at 55, G for A at 58, and C for T at 103. These changes eliminated three canonical AATAAA polyadenylation signals and introduced a PstI restriction site without altering the amino acid sequence encoded by the nucleotide sequence. pOG28 consists of a murine cDNA for dihydrofolate reductase cloned into pCDM8 (Aruffo and Seed, supra).

In the same samples, β-galactosidase activity was also proportional to the amount of FLP expression plasmid included (FIG. 2C). Only background activities were observed in cotransfections that included a non-FLP control plasmid (Table 1) or when pOG44 alone was transfected. The experiment thus provides both molecular and biochemical evidence for precise FLP-mediated recombination in mammalian cells.

Table 1 presents β-galactosidase activities in cotransfection assays of 293, CV-1, and F-9 cells. Positive control transfections (pFRTβGAL) included 1 μg of pFRTβGAL and 18 μg of the pOG28 non-FLP control plasmid; negative control transfections (pNEOβGAL) included 1 μg of pNEOβGAL and 18 μg of the pOG28; and experimental transfections (pNEOβGAL+FLP) contained 1 μg of pNEOβGAL and 18 μg of the pOG44 FLP expression plasmid (FIG. 1A). The column headed by "%" shows the pNEOβGAL+FLP values as a percentage of the pFRTβGAL positive control. Each value represents the mean for six plates from two experiments. Standard errors are in parentheses. Neither pOG28 nor pOG44 generated β-galactosidase activity when transfected alone. All transfections contained 1 μg of pRSVL [de Wet et al., Mol. Cell. Biol. 7:725 (1987)] to correct β-galactosidase activities for relative transfection efficiencies.

Subconfluent cultures of cells in 10 cm dishes and grown in Dulbecco's modified Eagle's medium (DMEM) and 5% calf serum were transfected by overnight exposure to calcium phosphate precipitates [Graham et al., Virology 36:59 (1979)] and then split 1:4. After 24 hours incubation, one plate of each transfection was harvested by Hirt extraction [J. Mol Biol. 24:365 (1967)] and a second plate was used to prepare cytoplasmic extracts [de Wet et al., supra]. Approximately 5% of the DNA recovered from single plates was used for Southern analyses. β-galactosidase assays were performed as described by Hall et al., in J. Mol. Appl. Genet. 2:101 (1983)]. Luciferase activities generated by the inclusion of 1 μg of pRSVL (de Wet et al., supra) in all transfections were used to correct β-galactosidase activities for relative transfection efficiencies. The experiment was repeated twice with similar results.

TABLE 1

β-GALACTOSIDASE ACTIVITIES (UNITS/ MG PROTEIN) IN COTRANSFECTED CELLS

| | TRANSFECTIONS | | | |
|---|---|---|---|---|
| CELL LINE | pFRTβGAL | pNEOβGAL | pNEOβGAL +FLP | % |
| 293 | 30.4 (1.9) | 0.17 (0.02) | 14.2 (2.2) | 47 |
| CV-1 | 275 (25) | 0.33 (0.06) | 22.6 (1.2) | 8 |
| F9 | 24.8 (4.3) | 0.04 (0.01) | 1.88 (0.02) | 8 |

FLP activity has also been demonstrated in monkey kidney (CV-1) and mouse embryonal carcinoma (F9) cells. In Table 1, the β-galactosidase activity in the "pFRTβGAL" transfections represents an estimate of the expression expected if all the pNEOβGAL in a co-transfection were immediately recombined. The highest β-galactosidase expression in co-transfections employing pNEOβGAL plus pOG44, relative to pFRTβGAL transfected cells, was 47%, seen in 293 cells. This is a remarkable level considering that β-galactosidase expression required both FLP expression, followed by recombination of pNEOβGAL, to produce a construct capable of expressing β-galactosidase. Co-transfections of CV-1 and F9 cells generated 8% of the activity seen in the pFRTβGAL transfections. Even at this lower relative activity, cotransfected cells were readily observed in histochemical reactions for β-galactosidase activity.

| Example 2 | FLP-Mediated Removal of Intervening Sequences |
|---|---|

If the invention method is to be widely applicable, for example for gene activation in transgenic mammals, the ability of FLP to faithfully promote precise recombination at FLP recombination target sites contained in the mammalian genome is required. Such ability is demonstrated in this example.

Figures 3A, 3B:
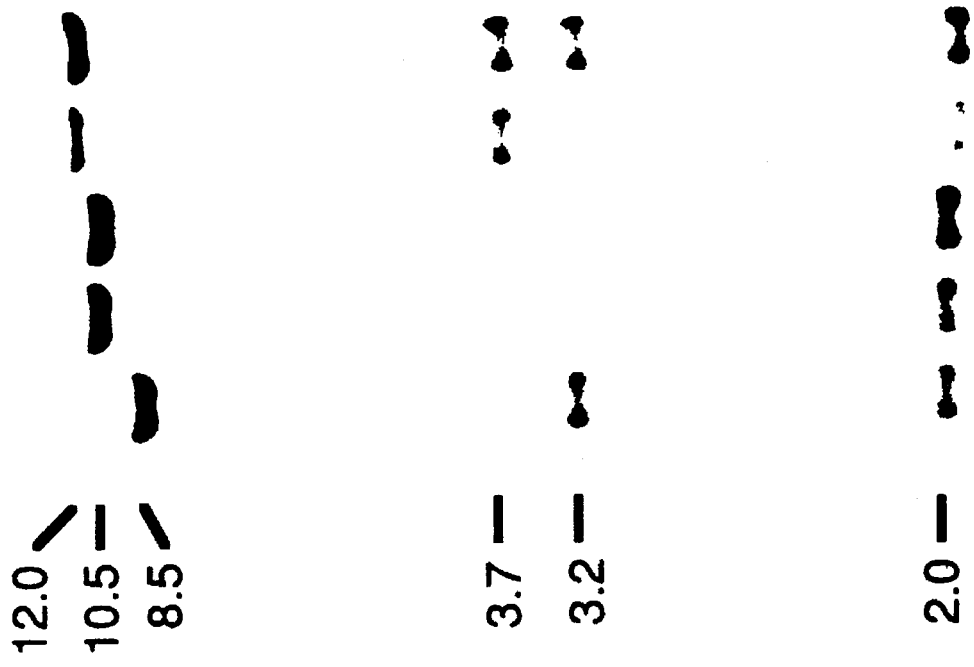
FIGS. 3A and 3B.

Cell lines that contain single integrated copies of pNEOβGAL (designated CVNEOβGAL/E) were produced by transfecting CV-1 cells with linearized plasmid by electroporation, then isolated by selecting G418-resistant (G418$^R$) transfectants that stably expressed the neomycin cassette, and finally identifying single copy lines by Southern blot analyses (FIG. 3). As previously shown for other integrated constructs with similarly short direct repeats, the chromosomal FRTs did not spontaneously recombine (in the absence of FLP) to produce a β-galactosidase-positive (βGAL$^+$) phenotype at detectable frequencies (Table 2).

Transient expression of FLP in the CVNEOβGAL/E lines (by transiently transfecting with the pOG44 FLP expression vector) promoted a rapid conversion to a βGAL$^+$ phenotype. When five different lines were transiently transfected with the pOG44 FLP expression vector, β-galactosidase activities at 36 hours were 40 to 100-fold higher than those seen in replicate plates transfected with a non-FLP plasmid (Table 2). At 48 hours after transfection histochemical processing showed many positive cells (Table 2).

Table 2 presents the β-galactosidase phenotypes of CVNEOβGAL/E lines, which contain a single copy of the β-galactosidase inactive reporter, pNEOβGAL, after transfection with FLP expression (pOG44), non-FLP negative control (pOG28) or β-galactosidase positive control (pFRTβGAL) plasmids. The pFRTβGAL transfections included 1 μg of pFRTβGAL and 19 μg of pOG44; other mixes contained 20 μg of the indicated plasmid. β-galactosidase activities are mean values for triplicate transfections performed as described for FIG. 2 and assayed 36 hours after removal of precipitates; standard errors for the pOG44 transfections were less than 10% of the mean. The percent positive was determined by scoring more than 103 cells after transfection and histochemical processing as described by de Wet et al., supra.

TABLE 2

β-GALACTOSIDASE PHENOTYPES OF TRANSFECTED CVNEOβGAL CELL LINES

| CELL LINE | ACTIVITIES (units/mg protein) | | PERCENT POSITIVE | | |
|---|---|---|---|---|---|
| | pOG28 | pOG44 | pOG28 | pFRTβGAL | pOG44 |
| E6 | 0.24 | 11.2 | 0† | 8.7 | 6.1 |
| E25 | 0.21 | 16.7 | 0† | 17.1 | 12.4 |
| E26 | 0.18 | 7.2 | 0† | 19.5 | 15.4 |
| E14 | 0.28 | 13.1 | ND | ND | ND |
| E22 | 0.09 | 9.6 | ND | ND | ND |

†No positive cells were found among ≦10$^6$ cells examined.
ND: Not done.

To provide some estimate of the efficiency of recombination, an additional set of replicate plates were transfected with the pFRTβGAL β-galactosidase expression vector. Comparing the fractions of cells that were βGAL+ in the pFRTβGAL and in the pOG44 transfections (assuming similar transfection efficiencies) suggests that most (70–80%) of the cells transfected with pOG44 were converted to a βGAL$^+$ phenotype (Table 2). The comparison undoubtedly underestimates the efficiency of FLP-mediated excision. Whereas many copies of a functional β-galactosidase gene were available for immediate transcription in the positive controls, recombination may have occurred shortly before harvest in some pOG44-transfected cells. In these cases the single recombined reporter gene may not have generated enough β-galactosidase by the time of harvest to render the cells positive in this assay.

The βGAL$^+$ phenotype was passed on to all descendant of many FLP-converted cells. Positive colonies were formed during prolonged expansion of individual colonies. Entirely negative colonies and mixed colonies were also observed. Mixed colonies would be expected if recombination occurred after mitosis in only one descendent of a transfected cell, or if recombined and unrecombined cells mixed at replating or during subsequent growth. Indeed, the physical segregation of phenotypes evident in most mixed colonies suggested that they were composed of stably positive and negative lineages.

The correlation between β-galactosidase expression and recombination at FRT sites was examined by comparing the structure of the integrated pNEOβGAL sequences in two βGAL$^+$ subclones to the parental line. CVNEOβGAL/E25 (106) cells were transfected with the pOG44 FLP expression vector and subcloned 12 hours after removal of the precipitate. After histochemical screening, two βGAL$^+$ subclones (E25B1 and E25B2) were expanded for further analysis. In Southern blots of genomic DNA from both subclones, the pattern of hybridization matched that expected for FLP-mediated recombination of the FRT sites in the parental line (FIG. 3). While recombination products have not been recovered and sequenced, these Southern analyses and the fact that activation of β-galactosidase expression required creation of a functional translational reading frame indicate that FLP-mediated recombination was precise.

| Example 3 | FLP Mediated Recombination of FRT on an Extrachromosomal Molecule With a Chromosomally Integrated FRT. |
|---|---|

Reversal of the process described in the previous Example, i.e., the FLP-mediated recombination of an FRT site on a plasmid with a chromosomally integrated FRT site, can be used to target the integration of transfected plasmids to specific genomic sites. To determine the frequency at which this occurs, G418-sensitive, βGAL$^+$ E25B2 cells were co-transfected with the pOG44 FLP expression vector and a plasmid, pOG45, that contained a neomycin resistance gene expression cassette and a single FRT. pOG45 consisted of the neomycin resistance cassette and 3' FRT from pNEOβGAL cloned into pUC19. 8×10$^5$ CVNEOβGAL cells were transfected by electropotation in 800 μl of saline containing 40 μg of pOG44 and 0.1 μg of either pOG45 or, for a negative control, pOG45A (which was derived from pOG45 by deleting a 200 bp fragment containing the FRT).

G418$^R$ subclones (designated B2N) from three transfections that had stably integrated pOG45 were histochemically stained for β-galactosidase activity and more than half (104 of 158, or ~66%) were either entirely β-galactosidase-negative (βGAL$^-$) or predominantly βGAL$^-$ with a few clusters of βGAL$^+$ cells. The remaining colonies were βGAL$^+$. With continued passage as dispersed monolayers, the fraction of βGAL$^+$ cells in the mosaic lines rapidly diminished. This suggested they were G418$^-$ sensitive cells that initially survived because of their proximity to resistant cells; this was confirmed by reconstitution experiments. All of the 55 colonies formed after parallel co-transfections of pOG44 and a derivative of pOG45 (pOG45A) that lacked an FRT were βGAL$^+$.

The correlation between loss of β-galactosidase activity and recombination between plasmid and chromosomal FRTs was examined in Southern analyses. Because the FRT and neomycin cassette of pOG45 were derived from the neomycin cassette and 3' FRT of pNEOβGAL (FIG. 2A), recombination of the plasmid FRT with the E25B2 chromosomal FRT regenerates the 3.2 kb EcoRI fragment of the original CVNEOβGAL/E25 parent. Additionally, the 8.5 kb junctional fragment of CVNEOβGAL/E25 shifts to 12.0 kb because pOG45 is 3.5 kb larger than the neomycin cassette of pNEOβGAL. The 3.2 kb EcoRI fragment and the 8.5 kb junctional fragment were observed in each of the 10 cell lines analyzed after initial histochemical classification as βGAL$^-$ or mosaic, as shown for two such lines in FIG. 3B. In contrast, each of the four βGAL+ colonies examined by Southern analyses showed that pOG45 had integrated at a random site.

These data show that FLP-mediated recombination will target the integration of transfected DNA to a specific chromosomal site at frequencies that exceed those of random integration, and that the event can be marked by the alteration in gene activity at the target site. The efficiency of targeted integration can be increased by standard optimization techniques, such as for example, by using ratios of the integrating plasmid and FLP expression vectors different from the single ratio mixture used here, or by using FRT mutations in the plasmid and chromosomal sites to decrease the frequency with which successfully integrated plasmids are subsequently excised.

While the invention has been described in detail with reference to certain preferred embodiments thereof, it will be understood that modifications and variations are within the spirit and scope of that which is described and claimed.

SUMMARY OF SEQUENCES

Sequence I.D. No. 1 is the approximately 1450 base-pair sequence encoding a FLP recombinase contemplated for use in the practice of the present invention, as well as the amino acid sequence deduced therefrom.

Sequence I.D. No. 2 is the amino acid sequence deduced from the nucleotide sequence of Sequence ID No. 1.

Sequence I.D. No. 3 is the nucleotide sequence of the FLP recombination target site (FRT).

Sequence I.D. No. 4 is the oligonucleotide sequence used for the construction of pFRTβGAL expression vector.

---

That which is claimed is:

1. A method for the integration of a first nucleic acid into the genome of a mammalian host cell, said method comprising:
   a) stably integrating a first FLP recombination target site (FRT) into said genome; and
   b) introducing into said mammalian host cell of step a) an FLP recombinase and said first nucleic acid, wherein said first nucleic acid comprises a second FRT, and wherein said FLP recombinase catalyzes recombination between said first FRT and said second FRT, thereby precisely targeting integration of said first nucleic acid into said genome at the site of said first FRT, thereby achieving the assembly or disassembly of a functional expression unit.

2. A method for excising the first nucleic acid that has been integrated into the genome of a mammalian host cell according to claim 1, said method comprising contacting said mammalian host cell with FLP recombinase, wherein said FLP recombinase catalyzes recombination between said first FRT and said second FRT, thereby excising said first nucleic acid from said genome.

3. A method according to claim 1, further comprising:
   c) further introducing into said mammalian host cell a second nucleic acid comprising a third FRT,
   wherein said second nucleic acid is introduced simultaneously with said first nucleic acid, or separately after said first nucleic acid,
   wherein an FLP recombinase may optionally be added along with said second nucleic acid, and
   wherein the FLP recombinase catalyzes recombination between said third FRT and said first or second FRT, thereby precisely targeting integration of said second nucleic acid into said genome.

4. A method for the site-specific integration of a first nucleic acid into the genome of a mammalian cell, wherein a first FRT is stably integrated in said genome, said method comprising:
   introducing into said mammalian cell an FLP recombinase and said first nucleic acid, wherein said first nucleic acid comprises a second FRT and a first segment of a gene of interest, and wherein said FLP recombinase catalyzes recombination between said first FRT and said second FRT, thereby precisely integrating said first nucleic acid at the site of said first FRT in said genome, thereby achieving the assembly or disassembly of a functional expression unit.

5. A method according to claim 4, wherein said gene of interest is present in said genome of said mammalian cell, and said first FRT is positioned within said gene of interest.

6. A method according to claim 4, comprising further introducing into said mammalian cell a second nucleic acid,
   wherein said second nucleic acid comprises a third FRT and either a second segment of said gene of interest or a first segment of another gene of interest;
   wherein said second nucleic acid is introduced simultaneously with said first nucleic acid, or separately after said first nucleic acid,
   wherein an FLP recombinase may optionally be added along with said second nucleic acid,
   wherein said FLP recombinase catalyzes recombination between said third FRT and said first or said second FRT,
   wherein said second nucleic acid specifically integrates in reading frame with said first nucleic acid, and
   wherein the FLP-mediated recombination provides a functional gene comprising said first nucleic acid and said second nucleic acid.

7. A method according to claim 4 wherein said FLP recombinase is provided by an FLP expression vector.

8. A method according to claim 7 wherein the expression of said FLP recombinase is regulated.

9. A method according to claim 4, comprising further introducing into said mammalian cell a second nucleic acid,
   wherein said second nucleic acid comprises a third FRT,
   wherein said second nucleic acid is introduced simultaneously with said first nucleic acid, or separately after said first nucleic acid,
   wherein an FLP recombinase may optionally be added along With said second nucleic acid,
   wherein the FLP recombinase catalyzes recombination between said third FRT and said first or said second FRT, and
   wherein the combination of said first nucleic acid and said second nucleic acid prevents expression of said gene of interest.

10. A method for the site-specific integration of transfected DNA into the genome of a transgenic mammal, wherein said genome comprises a first FRT, said method comprising contacting said genome with an FLP recombinase and a first DNA comprising a second FRT, under conditions suitable for site-specific integration of said first DNA into said genome at said first FRT, thereby achieving the assembly or disassembly of a functional expression unit.

11. A method according to claim 10 wherein said first DNA further comprises a first segment of a gene of interest, and wherein said genome is further contacted with a second DNA, wherein said second DNA comprises a third FRT and either a second segment of said gene of interest or a first segment of another gene of interest, and wherein said second DNA, when combined in reading frame with said first DNA, provides a functional gene comprising said first DNA and said second DNA.

12. A method according to claim 10 wherein said FLP recombinase is provided by an FLP expression vector.

13. A method according to claim 12 wherein the expression of said FLP recombinase is regulated.

14. A method according to claim 10 wherein said first FRT is within a functional gene, and is so positioned that the introduction of additional DNA sequences at said first FRT will inactivate said gene.

* * * * *